United States Patent [19]

Yamamoto

[11] Patent Number: 4,544,271

[45] Date of Patent: Oct. 1, 1985

[54] DENSITOMETER

[75] Inventor: Hiroshi Yamamoto, Nagaokakyo, Japan

[73] Assignee: Shimadzu Corporation, Kyoto, Japan

[21] Appl. No.: 444,703

[22] Filed: Nov. 26, 1982

[30] Foreign Application Priority Data

Nov. 28, 1981 [JP] Japan .................. 56-191599

[51] Int. Cl.⁴ .......................... G01J 3/18; G01J 3/42
[52] U.S. Cl. ..................................... 356/328; 356/320
[58] Field of Search ............... 356/308, 319, 320, 326, 356/328, 443, 444

[56] References Cited

U.S. PATENT DOCUMENTS 3,966,323 6/1976 Matsuoka et al. ................. 356/328
4,259,014 3/1981 Talmi ................................. 356/328

FOREIGN PATENT DOCUMENTS 54827 4/1982 Japan .................................. 356/319

OTHER PUBLICATIONS

Meyling et al., Journal of Physics E: Scientific Instruments, vol. 10, No. 5, May 1977, pp. 438–440.
Analytical Chemistry, vol. 50, No. 5, Apr. 1978, pp. 312R and 323R.

Primary Examiner—F. L. Evans
Attorney, Agent, or Firm—Fidelman, Wolffe and Waldron

[57] ABSTRACT

A densitometer wherein a sample to be measured is illuminated and the light transmitted through or reflected by the sample is passed through a slit and dispersed by a dispersing element so that a spectral image of the sample as defined by the slit is formed on the image plane of the dispersing element. A plurality of image sensors each comprising a linear array of photodiodes are disposed on the image plane in such a manner that each of the image sensors substantially conform to one of the images of the slit formed by different wavelengths. The outputs from the photodiodes are processed by a computer to provide desired information about the sample.

5 Claims, 11 Drawing Figures

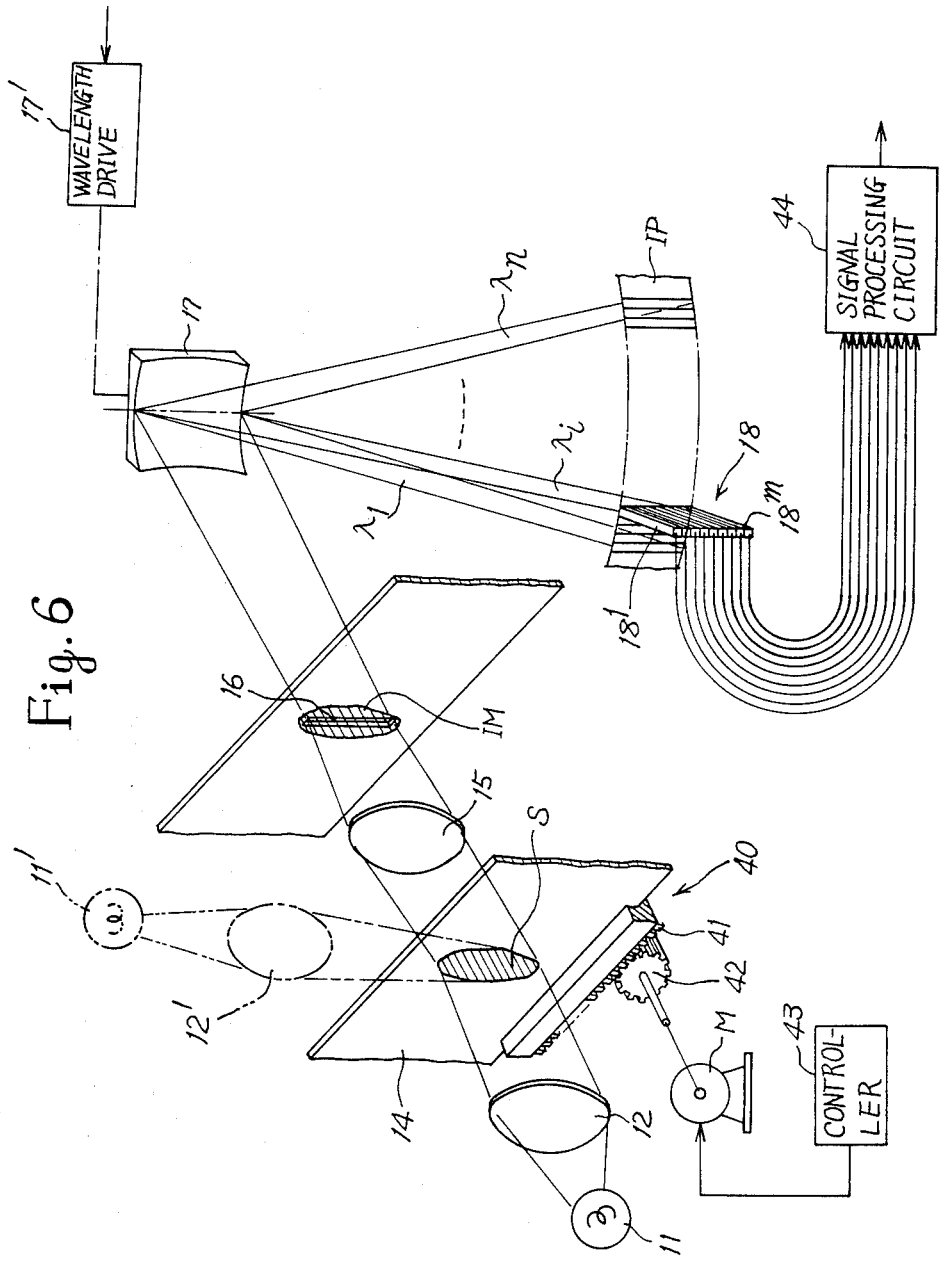

DENSITOMETER

BACKGROUND OF THE INVENTION

This invention relates to a new and improved densitometer which employs a solid-state image sensor as the detector.

The densitometer is an instrument used for quantitative measurement of a sample, such as a spot developed and separated on a support in thin-layer chromatography, which is commonly referred to as TLC. For measurement the sample spot is illuminated, and the light reflected by or transmitted through the spot is detected by a detector to produce a corresponding electrical signal, from which the density and consequently the quantity of the sample can be calculated.

Sample spots developed on a TLC plate differ in shape, thickness and size, and the distribution of the density of the sample components is not always uniform in each spot. In order to reduce error or inaccuracy in measurement caused by the nonuniformity of the density distribution in the spot it has been proposed to scan the whole area of the spot in a zigzag way by a thin light beam having a small cross section as compared with the area of the spot.

The method, however, requires a long time for measurement and a complicated mechanism for scanning, with a relatively low signal-to-noise ratio caused by the small cross section of the scanning light beam.

In recent years the solid-state image sensor which comprises an array of photodiodes has been developed and come to be used in densitometers as the detector. In the conventional densitometers, however, a photodiode array is arranged on the plane where the image of a sample is formed by the light that has passed a filter, which can provide only one wavelength.

Accordingly, the primary object of the invention is to provide a densitometer which uses a single or a plurality of image sensors as the detector in combination with a monochromator in such a manner as to enable free selection of wavelength.

Another object of the invention is to provide such a densitometer as aforesaid which makes it easy to perform dual-wavelength measurement.

Another object of the invention is to provide such a densitometer as aforesaid which is capable of measuring the density of a sample quickly and with a high degree of accuracy and precision.

Another object of the invention is to provide such a densitometer as aforesaid which is simple in structure, compact in size and low in manufacturing and maintenance cost.

Another object of the invention is to provide such a densitometer as aforesaid in which an electronic computer provides the measurement data in various desired forms.

BRIEF DESCRIPTION OF THE DRAWING

FIG. 6 is a schematic perspective view of another embodiment of the invention;

SUMMARY OF THE INVENTION

Briefly stated, in the densitometer of the invention a sample to be measured such as a spot developed on a TLC plate is illuminated by white light and the light transmitted through or reflected by the sample is collected by a lens to form an image of the sample on a slit. The light that has passed through the slit is dispersed by a dispersing element so that a spectral image of the sample as defined by the slit is formed on the image plane of the dispersing element. A plurality of image sensors each comprising a linear array of photodiodes are disposed on the image plane in such a manner that each of the image sensors substantially conforms to one of the images of the slit formed by monochromatic light of different wavelengths. The outputs from the photodiode arrays are processed by a computer to provide desired information about the sample.

DESCRIPTION OF THE PREFERRED EMBODIMENTS

Before describing a preferred embodiment of the invention, two typical conventional densitometers will first be explained with reference to FIGS. 1 and 2.

Figures 1, 2:
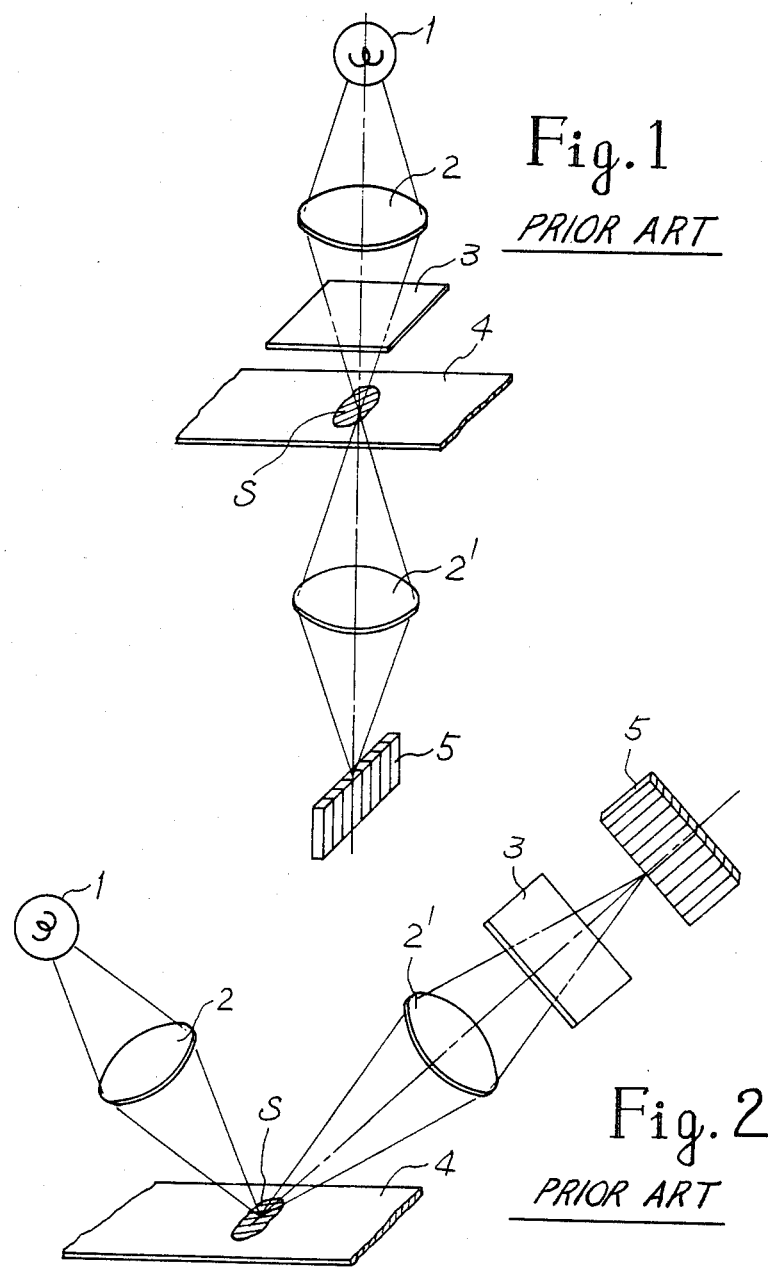
FIG. 1 is a schematic perspective view showing a general layout of a conventional densitometer in which the light transmitted through a sample is measured.
FIG. 2 is a view similar to FIG. 1 but showing another conventional densitometer in which the light reflected by a sample is measured.

In FIG. 1 the light transmitted through the sample is measured while in FIG. 2 the light reflected by the sample is measured. In the two figures the same reference numerals designate corresponding component parts.

There is shown a source of light 1 such as a tungsten lamp or a xenon lamp. The light from the source 1 is collected by a condenser lens 2. A filter 3 passes a selected wavelength of the light from the lens 2, which illuminates a sample spot S developed on a TLC plate 4. The light transmitted through the sample S is again collected by a condenser lens 2' which forms the image of a sample spot S on an image sensor 5 comprising an array of photodiodes, the output from which depends upon the concentration of the sample in the spot S. With the arrangement of FIG. 1, it is possible to detect the absorption characteristic of the sample with respect to the wavelength selected by the filter 3.

In FIG. 2, the light reflected by a sample S on a TLC plate 4 is collected by a condenser lens 2' and then passed through a filter 3 so as to be detected by an image sensor 5.

In the conventional devices, the image sensor is disposed on the plane of the image of the sample formed by the light that has passed the filter 3, which can provide only one wavelength.

The image sensor has various advantages such as that the component photoelectric elements are very small in size, that the elements can be arranged in an array or in such a manner as to provide a photosensitive plane surface, and that the sensor is quick in response.

The invention makes the best use of these and other advantages of the image sensor and provides a densitometer which can be combined with an electronic computer to perform various functions.

Figure 3:
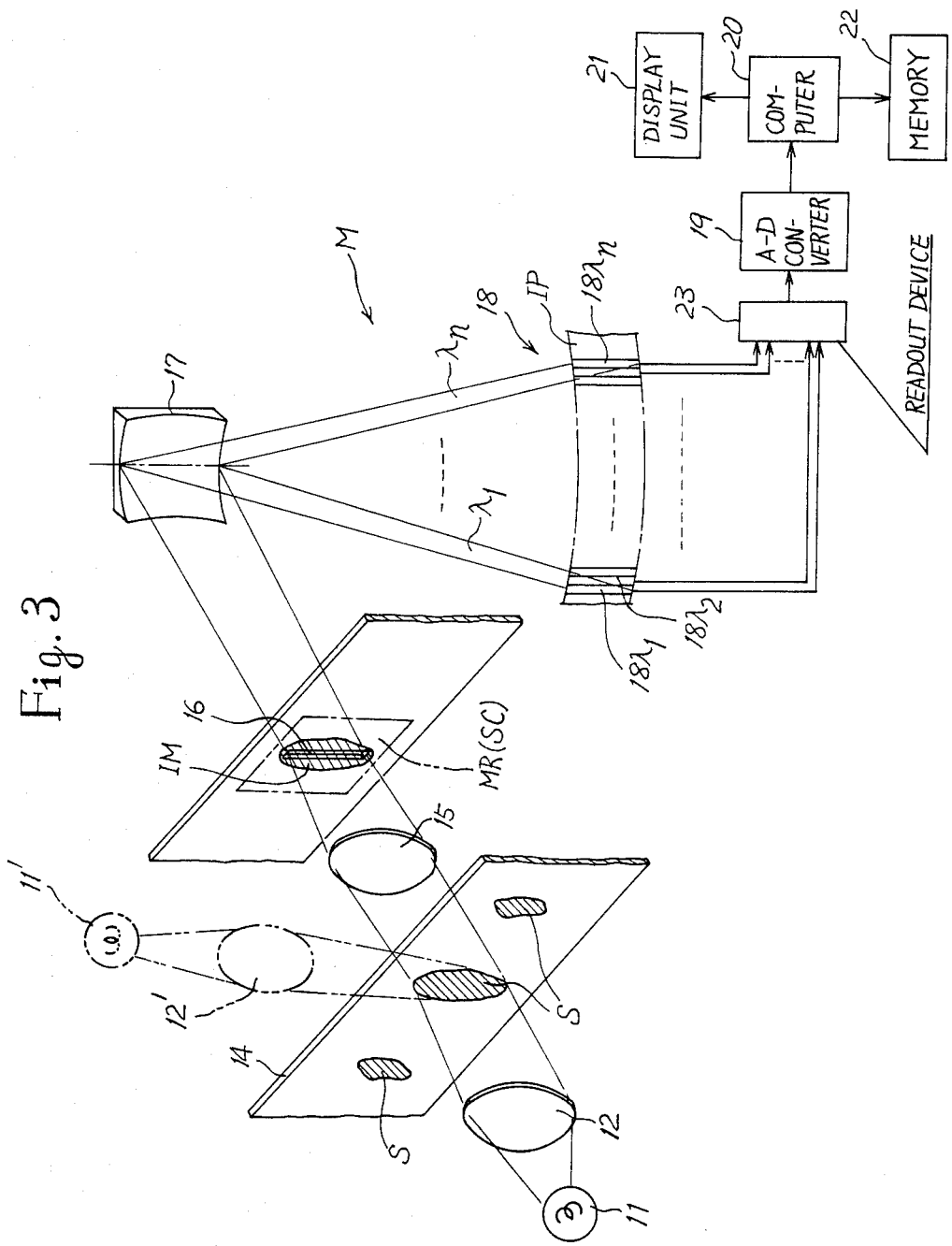
FIG. 3 is a schematic view showing a general layout of one embodiment of the invention.

Turning to FIG. 3, which shows one embodiment of the invention, there is shown a source of light 11 such as a tungsten lamp or a xenon lamp. The light from the source 11 is collected by a condenser lens 12 and projected onto a sample spot S developed on a TLC plate 14. Part of the light is absorbed by the sample, the amount absorbed depending upon the concentration of the sample.

Instead of, or in addition to, the light source 11 and the lens 12 there may be provided another light source 11' and another condenser lens 12', so that the light reflected by the sample can be measured.

The light transmitted through or reflected by the sample is focussed by an image forming lens 15 so as to form an image IM of the sample spot S at an entrance slit 16 of a monochromator M.

The light that has passed through the slit 16 is dispersed by a concave diffraction grating 17 into different wavelengths $\lambda_1, \lambda_2, \ldots, \lambda_n$, which form a spectral image of the sample as defined by the entrance slit 16 on an image plane IP.

On the image plane IP there is provided a detector 18 which comprises a plurality of image sensors $18\lambda_1, 18\lambda_2, \ldots, 18\lambda_n$ arranged side by side at those positions on the image plane IP which correspond to the different wavelengths $\lambda_1, \lambda_2, \ldots, \lambda_n$, so that each of the image sensors receives the light of the corresponding one of the wavelengths. For simplicity of illustration the image sensors are schematically shown as a series of mere stripes in FIG. 3.

The output of each of the image sensors is read out by a readout device 23 and put into an A-D converter 19, which converts analog input signals to corresponding digital output signals.

An electronic computer 20 processes the digital signals and the processed data are displayed on a display unit 21 and/or stored in a memory 22.

If the absorbance of the sample is to be measured, a logarithmic converter not shown in FIG. 3 is connected between the readout device 23 and the A—D converter 19 so that the A-D conversion is preceded by logarithmic conversion of the readout data.

Figure 4:
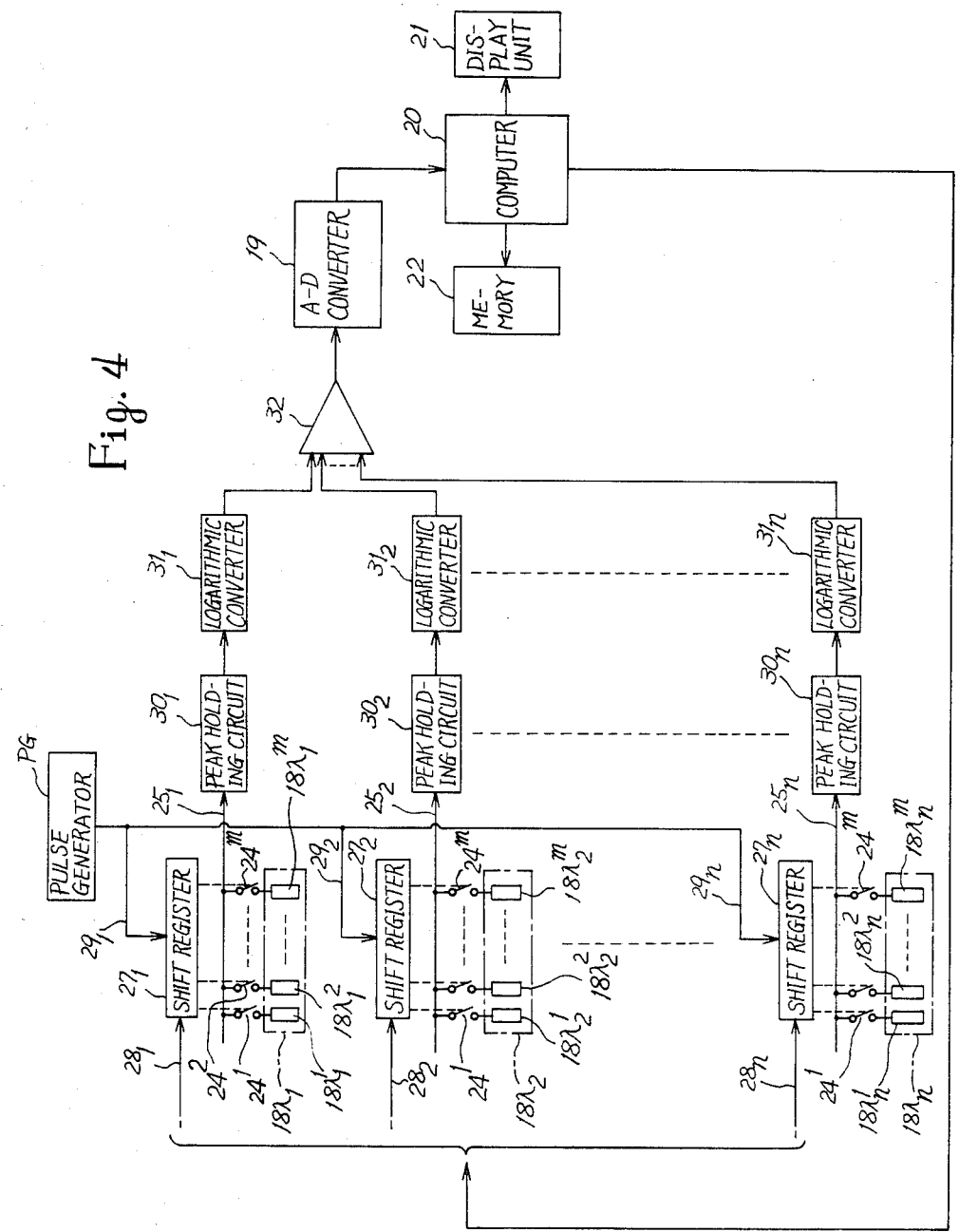
FIG. 4 is a block diagram of one example of the readout device shown as a block in FIG. 3.

FIG. 4 shows by way of example the concrete arrangement of the readout device 23 shown in FIG. 3. The image sensor $18\lambda_1$ comprises an array of photodiodes $18\lambda_1{}^1, 18\lambda_1{}^2, \ldots, 18\lambda_1{}^m$; similarly the image sensor $18\lambda_2$ comprises an array of photodiodes $18\lambda_2{}^1, 18\lambda_2{}^2, \ldots, 18\lambda_2{}^m; \ldots$; and the image sensor $18\lambda_n$ comprises an array of photodiodes $18\lambda_n{}^1, 18\lambda_n{}^2, \ldots, 18\lambda_n{}^m$.

A first group of switches $24^1, 24^2, \ldots, 24^m$ are connected between a common readout line $25_1$ and the photodiodes $18\lambda_1{}^1, 18\lambda_1{}^2, \ldots, 18\lambda_n{}^m$, respectively, of the first image sensor $18\lambda_1$. Similarly a second group of switches $24^1, 24^2, \ldots, 24^m$ are connected between a second common readout line $25_2$ and the photodiodes $18\lambda_2{}^1, 18\lambda_2{}^2, \ldots, 18\lambda_n{}^m$ of the image sensor $18\lambda_2$. In this manner, an $n$th group of switches $24^1, 24^2, \ldots, 24^m$ are connected between an $n$th common readout line $25_n$ and the photodiodes $18\lambda_n{}^1, 18\lambda_n{}^2, \ldots, 18\lambda_n{}^m$, respectively, of the $n$th image sensor $18\lambda_n$.

Shift registers $27_1, 27_2, \ldots, 27_n$ control the switching operation of these groups of switches. A pulse generator PG applies clock pulses to the shift registers $27_1$ to $27_n$ through lines $29_1, 29_2, \ldots, 29_n$, respectively. When the computer 20 applies a start signal to the selected one of the shift registers $27_1, 27_2, \ldots, 27_n$ or one of the shift registers after another successively through lines $28_1, 28_2, \ldots, 28_n$, respectively, the switches $24^1, 24^2, \ldots, 24^m$ are operated so that the outputs from the photodiodes $18\lambda_n{}^m$ (wherein $m$ and $n$ represent an integer, respectively) are applied as video signals to peak holding circuits $30_1, 30_2, \ldots, 30_n$, respectively, which hold the highest value of the video signals from the photodiodes constituting each of the image sensors, or all signal values from the photodiodes, or the average of all those signal values.

The signals held in the peak holding circuits $30_1$ through $30_n$ are applied to logarithmic converters $31_1$ through $31_n$, which produce corresponding absorbance signals. These signals are amplified by the amplifier 32 and then applied to the A-D converter 19.

The output from the A-D converter 19 is further processed by the computer 20 as previously described with reference to FIG. 3.

Since the image sensors $18\lambda_1$ to $18\lambda_n$ are arranged in a plane, each comprising an array of photoelectric elements, by reading out the output from each of the photoelectric elements and processing the read out data it is possible to measure the density distribution of the sample in the area of each spot and display the measured data like contour lines in a geographical map.

Since the outputs from the image sensors $18\lambda_1, 18\lambda_2, \ldots, 18\lambda_n$ correspond to wavelengths $\lambda_1, \lambda_2, \ldots, \lambda_n$, respectively, it is possible to perform a dual-wavelength measurement by taking out the outputs of those two of the image sensors which correspond to two selected wavelengths.

In the above described embodiment of the invention, the TLC plate is kept fixed or stationary. If there are developed on a TLC plate two or more sample spots spaced apart from each other, the plate may be moved in one direction so that the spots can be analyzed one after another.

Figure 5:
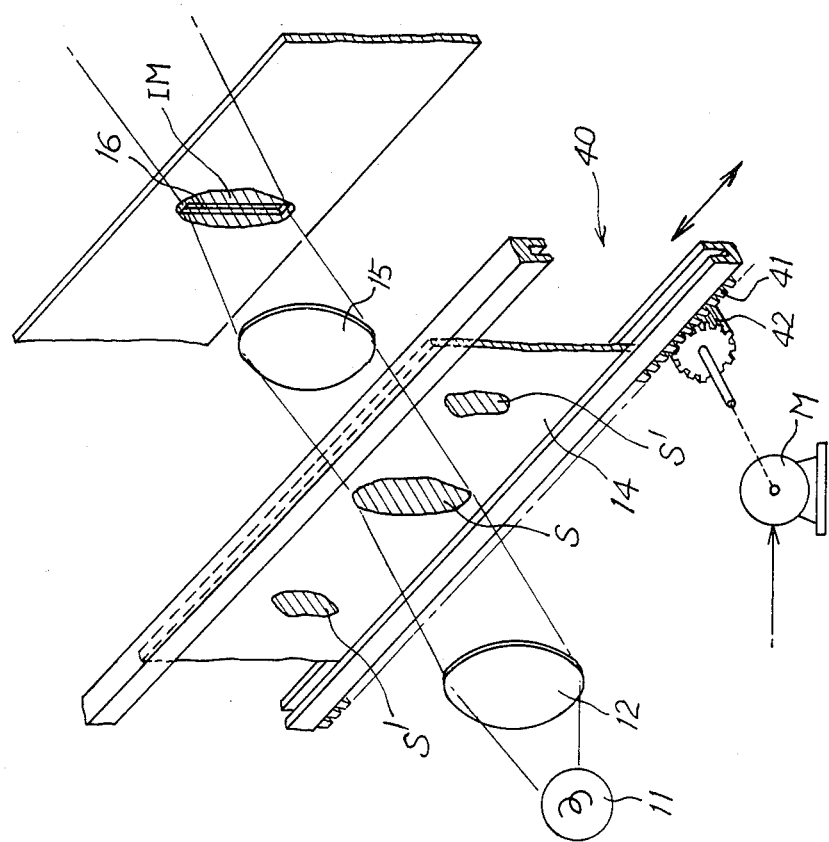
FIG. 5 is a schematic perspective view showing an example of the mechanism for moving the TLC plate relative to the entrance slit.

To this end as shown in FIG. 5 the TLC plate 14 may be carried by a frame 40 provided on one longitudinal side thereof with a rack 41 meshing with a drive pinion 42 driven by a pulse motor M. The computer 19 applies control pulses to the motor M, which rotates the pinion 42 stepwise so as to displace the frame 40 and the LTC plate 14 thereon a predetermined distance thereby to replace the sample spot S by the next sample spot S'.

FIG. 6 shows another embodiment of the invention, wherein only one image sensor 18 comprising a single array of photodiodes $18^1, 18^2, \ldots, 18^m$ is employed. In FIG. 6 the same reference numerals as in FIGS. 3 to 5 designate corresponding parts or elements. In this embodiment, the TLC plate 14 is moved relative to the entrance slit 16 and consequently the image sensor 18 in such a manner that the whole area of the sample spot S or its image IM is scanned from one to the other end of the spot or image in the direction of movement thereof.

Figure 7A:
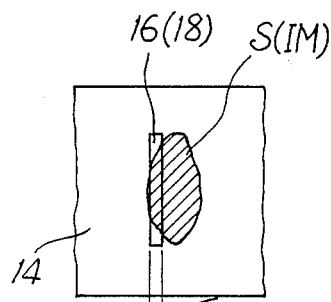
FIGS. 7a through 7d are schematic front views showing the relative positions of the image of a sample spot and the slit or the image sensor as the spot is moved relative to the slit or the image sensor.
Figure 7B:
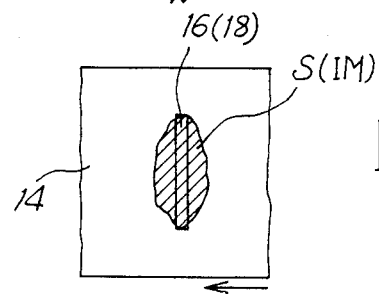
Figure 7C:
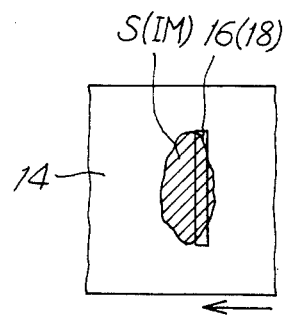
Figure 7D:
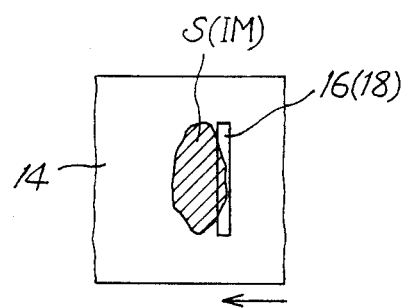

To put it in detail, the TLC plate 14 is incessantly moved a distance corresponding to the width W of the entrance slit 16 or the image sensor 18 at one time so that the relative position of the sample spot and the slit or image sensor changes as shown in FIGS. 7a through 7d, that is, from the position of FIG. 7a through the positions of FIGS. 7b and 7c to the position of FIG. 7d. A controller 43 applies appropriate signals to the pulse motor M so as to effect the stepwise movement of the TLC plate 14 with the sample spot S thereon.

Figure 8:
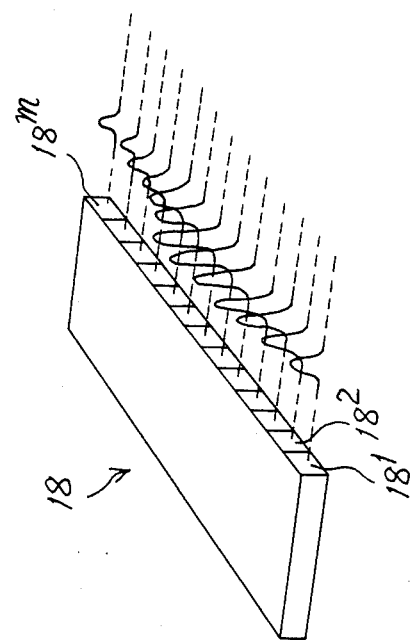
FIG. 8 is a schematic view showing the outputs of the image sensor as the sample spot is moved in the manner shown in FIGS. 7a through 7d.

The scanning of the sample spot in the above manner causes the photodiodes $18^1$ to $18^m$ of the single image sensor 18 to produce corresponding outputs as schematically shown in FIG. 8, which are applied to a signal processing circuit 44, from the output of which it is possible to know the density distribution of the sample in a spot developed in the direction of the movement of the image sensor or the TLC plate. A wavelength control device 17' is provided to rotate the grating 17 for wavelength scanning. A recorder and/or display unit may be provided to record and/or display the density distribution of the measured sample spot.

The above operation of the instrument of FIG. 6 may be conducted by the instrument of FIGS. 3 to 5 by scanning the whole area of one sample spot, and causing the computer to read out and process the outputs of all the component photodiodes of a selected one of the image sensors.

Thus, in accordance with the invention, a sample to be measured is illuminated by white light and the image of the sample is formed at the entrance slit of a monochromator. Part of the image is introduced into the monochromator, wherein a dispersing element disperses the introduced light to form a spectral image of the sample as defined by the entrance slit. On the image plane there is provided a single image sensor comprising a linear array of photodiodes, or a plurality of such image sensors arranged side by side to form a light-receiving surface, with the single image sensor or each of the image sensors conforming to one of the images of the entrance slit formed by different wavelengths. The illuminated sample is moved at predetermined intervals relative to the entrance slit of the monochromator perpendicularly to the longitudinal direction thereof, so that the outputs from the component photoelectric elements of the single image sensor or each of the group of image sensors are taken out as absorption or fluorescence signals, which are processed by an electronic computer to provide desired data.

In the above described embodiment, sample spots developed on a TLC plate are measured. The invention is not restricted to such sample spots, but various other objects such as a solution can also be measured.

In the illustrated embodiments, the image sensors are arranged on the image plane of the diffraction grating in such a manner that they correspond to the wavelengths of the spectrum, and for selection of wavelengths the outputs from those of the image sensors which correspond to the desired wavelengths are taken out at the processing stage in the computer. It is also possible to move a single image sensor along the spectral image plane, with the diffraction grating being held stationary, or to rotate the diffraction grating for wavelength scanning.

To enable observation of the image of the sample spot formed on the entrance slit from outside the instrument, the slit may be formed in a plane mirror MR shown in phantom in FIG. 3 so that the image IM of the sample spot formed on the plane mirror about the slit 16 may be reflected by the mirror and the reflected image may be observed through an eye piece. Alternatively, the entrance slit may be provided with a white screen SC so that the image of the spot being measured can be observed on the screen directly with a naked eye.

The width of the entrance slit of the monochromator may be variable so as to enable measurement of a desired part of the sample spot.

What I claim is:

1. A densitometer comprising:
   means for supporting a sample to be measured;
   an entrance slit adjacent said sample supporting means;
   means for illuminating said sample and projecting an image of said sample onto said slit;
   means for spectrally dispersing an image section, passing through and defined by said slit, into corresponding spectral lines on an image plane; and
   at least one photodiode linear array disposed on said image plane so as to substantially conform to a particular one of said spectral lines at a particular frequency, such that each diode of said linear array receives and senses an amount of light of a corresponding segment of said particular spectral line and outputs a signal level accordingly to a computer for processing said signal levels;
   whereby a density measurement of said image section; at at least one frequency, is provided.

2. The densitometer of claim 1, wherein said dispersing element is a diffraction grating.

3. The densitometer of claim 1, further including means for displaying the processed data provided by said computer.

4. A densitometer as in claim 1, and further comprising:
   at least one other of said photodiode linear arrays disposed on said image plane and substantially conforming to another of said spectral lines, such that dual-wavelength measurement of said image section is provided.

5. A densitometer as in claim 1, and further comprising:
   a plurality of said photodiode linear arrays arranged side by side and disposed on said image plane to form a light receiving surface so that each of said spectral lines is substantially conformed to by a corresponding one of said photodiode linear arrays; and
   means for providing incremental relative movement between said slit and said sample image such that a successive plurality of said image sections correspond to adjacent portions of said sample image.

* * * * *